(12) United States Patent
Batchelor et al.

(10) Patent No.: US 6,558,379 B1
(45) Date of Patent: May 6, 2003

(54) ELECTROSURGICAL SYSTEM

(75) Inventors: Kester J. Batchelor, Newport (GB);
Philip W. Hales, Rogerstone (GB);
Timothy O. W. Waterfield, Winchester (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/442,750

(22) Filed: Nov. 18, 1999

(51) Int. Cl.$^7$ ............................................. A61B 18/18
(52) U.S. Cl. ............................ 606/41; 606/50; 604/21
(58) Field of Search ..................... 606/41–50; 600/114, 600/125, 156; 604/21

(56) References Cited

U.S. PATENT DOCUMENTS

| | | | |
|---|---|---|---|
| 4,610,242 A | * 9/1986 | Santangelo et al. | 600/114 |
| 5,037,386 A | * 8/1991 | Marcus et al. | 604/43 |
| 5,197,963 A | * 3/1993 | Parins | 606/41 |
| 5,261,905 A | 11/1993 | Doresey, III | |
| 5,300,069 A | 4/1994 | Hunsberger et al. | |
| 5,429,596 A | 7/1995 | Arias et al. | |
| 5,451,223 A | 9/1995 | Ben-Simhon | |
| 5,707,351 A | 1/1998 | Dorsey, III | |
| 5,776,092 A | 7/1998 | Farin et al. | |
| 5,810,809 A | 9/1998 | Rydell | |
| 5,902,264 A | 5/1999 | Toso et al. | |
| 5,904,681 A | 5/1999 | West, Jr. | |
| 5,941,876 A | 8/1999 | Nardella et al. | |
| 6,027,502 A | 2/2000 | Desai | |
| 6,105,581 A | * 8/2000 | Eggers et al. | 128/898 |
| 6,126,592 A | * 10/2000 | Proch et al. | 600/114 |
| 6,196,967 B1 | * 3/2001 | Lim et al. | 600/125 |

FOREIGN PATENT DOCUMENTS

| | | |
|---|---|---|
| EP | 0 754437 | 1/1997 |
| WO | WO 97/00646 | 1/1997 |
| WO | WO 97/48345 | 12/1997 |

\* cited by examiner

Primary Examiner—Roy D. Gibson
(74) Attorney, Agent, or Firm—Nixon & Vanderhye P.C.

(57) ABSTRACT

An electrosurgical system includes an electrosurgical generator to which the active and return electrodes (18, 20) of an electrosurgical instrument (12) are connected. In use the electrodes are immersed in electrically-conductive fluid to complete a conduction path between them. The electrodes (18, 20) are located on a shaft (16) of the instrument which extends from a handle (14). The shaft is covered in a translucent flexible sheath (50) comprising a tube (60) having a large proximal opening (62) to enable insertion of the instrument within the sheath, and a narrower distal opening (64) through which the distal end of the instrument shaft projects, thereby to expose the active electrode (18) to the electrically-conductive fluid. Suction is applied to the interior of the sheath at an outlet port (66), and a seal (72) at the proximal end of the tube cooperates with a proximal surface (74) on the instrument handle to form a fluid-tight seal so that the suction is transmitted to the distal opening, in order to suck bubbles and debris away from the region around the active electrode (18). The distance between the active electrode (18) and the distal opening (64) of the tube (60) is chosen so that sufficient bubbles are sucked from the region around the active electrode to enable clear viewing of a treatment site without causing the resultant flow of conducting fluid over the active electrode to quench a vapor pocket which is formed around the active electrode when the instrument (12) is used to vaporize tissue.

30 Claims, 3 Drawing Sheets

Fig.8.

ELECTROSURGICAL SYSTEM

The present invention relates to an electrosurgical system, and in particular to an electrosurgical system which is used in a n environment where fluid is present during use.

Electrosurgery typically involves the use of radio frequency (RF) alternating currents to modify body tissue. Usually during electrosurgery the RF currents are passed through tissue at a treatment site, either killing the tissue and at the same time causing it to dissociate into tiny fragments (known in the art as vaporisation), or creating substantial heat at or nearby the treatment site to coagulate proteins from which tissue is made, and possibly also subsequently to desiccate the tissue. Vaporisation is a technique used either to cut tissue, in which case a relatively small channel of tissue separating two tissue masses is vaporised to enable parting of the tissue masses, or to ablate tissue, a process in which relatively large volumes of tissue at a treatment site are vaporised, which may for example result in the creation of a crater in the tissue. A coagulation procedure is typically performed to staunch the flow of blood from bleeding tissue, while depending upon the temperature to which the tissue at the treatment site is raised during coagulation, a desiccation procedure may follow inevitably subsequent to the coagulation, and involves heating the tissue to a point where moisture is driven out of the tissue, causing it to shrink as a result.

The application of electrosurgical techniques has advantages over traditional forms of surgery, in that, by using electrosurgery, a larger range of procedures may be performed using minimally-invasive surgical techniques. In addition, the ability to coagulate subsequent to, for example, the removal of a tissue mass reduces post-operative bleeding and results in shorter healing times.

Traditionally there are two forms of electrosurgery. Monopolar electrosurgery involves the delivery of RF power to a treatment site from an electrode on an electrosurgical instrument which is manipulated by a surgeon during the surgical procedure. Alternating current supplied from an electrosurgical generator flows through the patient's body between the electrode on the instrument and a further electrode, which is usually an electrically-conductive plate located in contact with the outside of the patient's body. Because the current density is only relatively high in the immediate vicinity of the electrode on the instrument, the passage of current through the patient's body to the external plate does not cause the modification of tissue in regions remote from the electrode on the instrument, and therefore the treatment site. Thus, it is only the electrode on the instrument which may said to be "active", i.e. modifies tissue.

In a bipolar system, the instrument has two or more electrodes, and current passes between the electrodes in a region local to the treatment site. In one form of bipolar electrosurgical system, unwanted tissue damage is avoided by constructing a bipolar instrument with an active or tissue treatment electrode, and a "return" electrode. The active electrode has a substantially smaller surface area than the return electrode, as a consequence of which the current density in the region of the active electrode is correspondingly higher than in the region of the return electrode. Since the magnitude of the current density determines whether tissue modification takes place, tissue in the region of the active electrode will experience modification as a result of the passage of current between the electrodes, whereas tissue in the region of the return electrode will not.

Both monopolar and bipolar electrosurgery are frequently performed in the presence of a liquid supplied to the treatment site. The liquid may be non-conductive, such as distilled water, glycine or sorbitol, in which case current passes between the electrodes only via tissue, meaning that, under normal conditions, both electrodes must be in contact with the tissue to enable current to flow. Alternatively, the liquid may be conductive, such as normal saline, in which case any conduction path between the electrodes will most likely include the liquid. In each case, the performance of electrosurgical procedures in the presence of a liquid can result firstly in the presence of tissue debris floating within the liquid, and secondly of bubbles within the liquid, both of which may obscure the surgeon's view of the treatment site (which, since the surgery is likely to be minimally invasive will most likely be provided by means of a remote viewing device, such as an endoscope or some other form of fibre-optic link).

A bipolar electrosurgical instrument is known from International Patent Application WO 97/00646 having a coaxial supply channel by means of which electrically-conductive fluid may be supplied to the treatment site, and a central return channel by means of which fluid and tissue debris may be removed from the treatment site. In use, saline fluid is fed down the supply channel under gravity, and removed along the return channel under suction.

The present invention provides an alternative to the prior art instrument, which inter alia enables existing instruments to be employed in operative environments where it is desirable to provide suction in the region of the treatment site.

A first aspect of the present invention provides an electrosurgical system comprising an electrosurgical instrument having a handle defining a proximal end of the instrument and by means of which the instrument may be manipulated by a user; a shaft extending from the handle; and an active tissue treatment electrode on the shaft which is axially spaced from the handle and which defines a distal end of the instrument; the system further comprising an elongate removable sheath adapted to extend coaxially with, and externally around, the shaft of the instrument, the sheath comprising an outlet port, an opening on the distal side of the outlet port, and sealing means on the proximal side of the outlet port for forming a substantially fluid-tight seal with the instrument, thereby to enable low pressure applied at the outlet port to be transmitted to the opening to create suction in the region of the opening.

The sheath may be optionally employed as desired depending upon whether removal of fluid and/or debris from the treatment site is desirable during the procedure to be performed. For example, it may be desirable to omit the sheath if a coagulation or a desiccation operation is to be performed, but to employ the sheath during vaporisation where significant amounts of bubbles and/or debris are created.

In a preferred embodiment, the sealing means cooperates with the shaft of the instrument to form the fluid-tight seal. In an alternative embodiment, however, a seal may be formed between cooperating surfaces provided by, for example, a part of the handle and an appropriately configured surface at the proximal end of the sheath.

In certain electrosurgical systems, and in particular in systems which are designed to operate in the presence of electrically-conductive fluid, the power applied to the instrument in order to achieve vaporisation requires very precise control, and is critically dependent upon the formation of a vapour pocket around the active electrode. In such systems, the sucking of fluid and/or debris away from the treatment site may have the effect of causing the flow of fluid over the active electrode as a result of the applied suction to remove heat so rapidly as to quench the vapour pocket, thereby rendering the instrument incapable of vaporisation while suction is applied. Preferably, therefore, in circumstances where the instrument and sheath are to be used for vaporisation, means will be provided for locating the opening on the sheath at a predetermined distance away from the active electrode. For a given flow rate at the outlet port of the sheath and power dissipation at the active electrode, the opening in the sheath may thus be positioned sufficiently far from the active electrode to prevent quenching of the vapour pocket, and yet sufficiently close to provide the requisite suction for the removal of liquid and/or debris. In one embodiment, the opening in the sheath is located by means of an abutment between two mutually-engageable surfaces on the sheath and the instrument. Preferably, the abutment will be between the handle of the instrument and an abutment surface in the region of the proximal end of the sheath.

In a preferred embodiment, the internal diameter of the sheath is larger towards the proximal end in the region of the outlet port than it is at the distal end in the region of the opening. This has a number of advantages. Firstly, it enables a relatively low flow rate applied by, for example, a vacuum pump connected to the outlet port to be translated into a substantial pressure drop at the opening; the low flow rate means that the opening may be positioned relatively close to the active electrode without quenching any vapour pocket which may be present, while the resultant high pressure drop provides powerful suction in the region of the treatment site. Secondly, in the event that blockage occurs in the lumen between the electrode shaft and the sheath, the instrument may be retracted within the sheath until the clearance between the instrument shaft and the sheath becomes sufficiently large (as a result of the greater internal diameter of the sheath towards the proximal end thereof) to enable the material causing the blockage to pass between the shaft and the sheath under the action of the suction applied at the outlet port.

In a preferred embodiment, the sheath is translucent, to enable easy visualisation of the passage of bubbles and/or debris from the treatment site. This enables a user to determine if the sheath is blocked, whereupon retraction of the sheath as described above may be performed to enable the blockage to be cleared.

In yet a further embodiment, the sheath is made of a relatively flexible material. This avoids limiting the range of procedures for which the instrument may be employed as a result of its size; if the sheath is flexible, then it is capable of deforming when the shaft of the instrument is inserted into relatively confined spaces.

All aspects of the electrosurgical system and elements thereof described and illustrated herein are equally applicable to monopolar and bipolar electrosurgical systems.

Yet a further independent aspect of the present invention provides a method of operating an electrosurgical system comprising an electrosurgical instrument having a handle at a proximal end thereof by means of which the instrument may be manipulated, a shaft extending from the handle on which an active tissue treatment electrode is located at a distal end of the instrument, and an electrosurgical generator connected to the active electrode to supply radio frequency power thereto, the method comprising the steps of:

sheathing at least a part of the shaft of the instrument in a substantially fluid-tight chamber, the chamber having an opening located in the vicinity of the active electrode;
immersing the active electrode within a liquid;
operating the generator to apply radio frequency power to the active electrode; and
reducing pressure within the chamber, thereby creating suction at the opening in the region of the active electrode.

Typically, the method will be performed using a bipolar instrument which additionally has a return electrode located on the shaft, with both the active and return electrodes being immersed in an electrically-conductive fluid which completes the conduction path between the electrodes. In one embodiment of the method, the generator is operated to apply power to the active electrode to cause it to operate in vaporisation mode whereby a vapour pocket is created around the active electrode, and the suction at the opening of the chamber does not create a sufficient flow of liquid over the active electrode to quench the vapour pocket.

Although the use of a sheath as described herein may be employed to remove bubbles and/or tissue debris from a treatment site, it may equally be employed for other purposes such as the supply of fluid to a treatment site, or to provide suction for a purpose other than removal of bubbles and/or tissue debris.

Embodiments of the invention will now be described, by way of example, and with reference to the accompanying drawings, in which.

Figures 1, 3, 4, 5, 6:
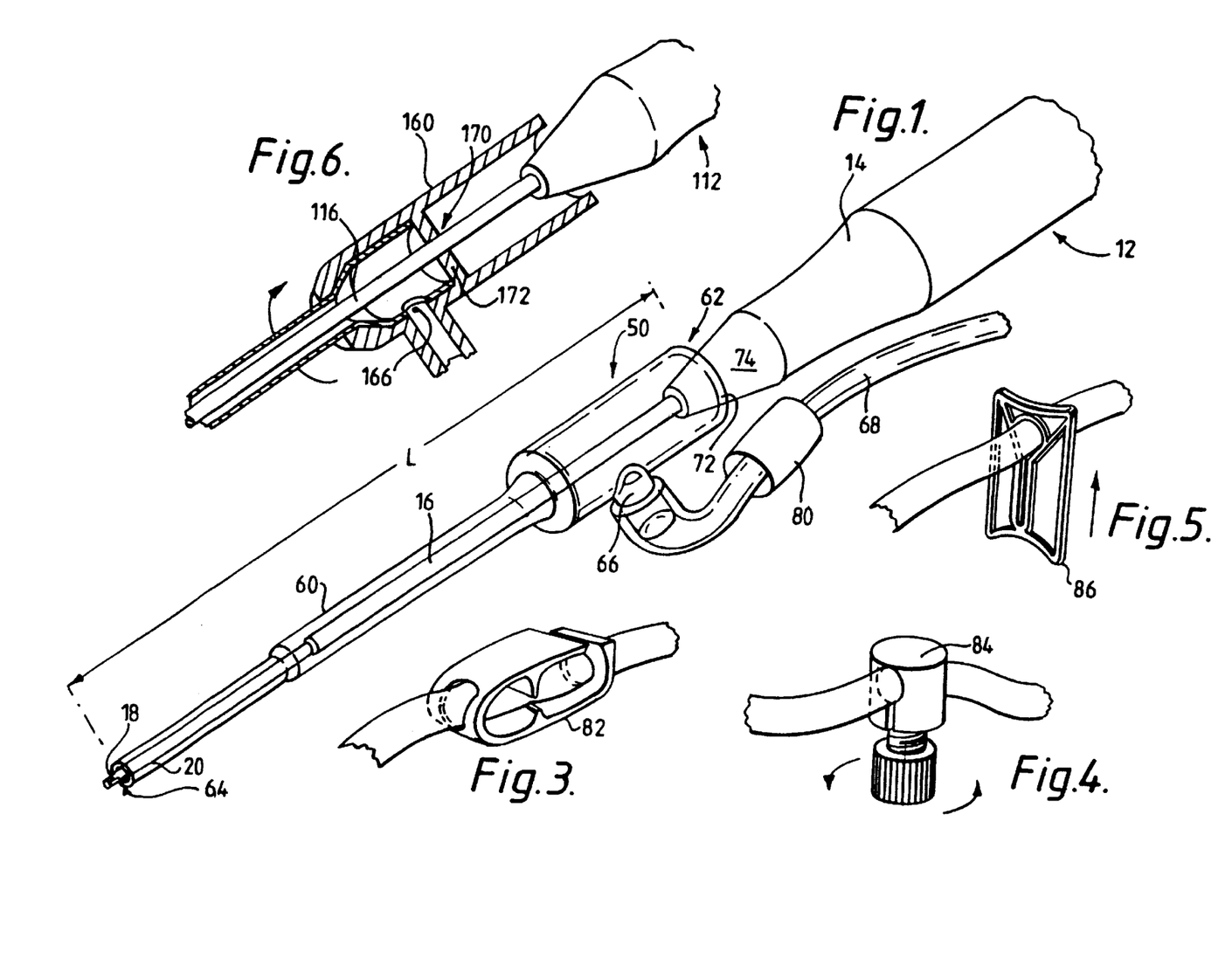
FIG. 1 is a perspective view of an embodiment of electrosurgical system according to the present invention.
FIG. 3 is a further detail of FIG. 1.
FIGS. 4 and 5 are modifications to the detail of FIG. 3.
FIG. 6 is a detail of an alternative design of sheath.
Figures 2, 7A, 7B:
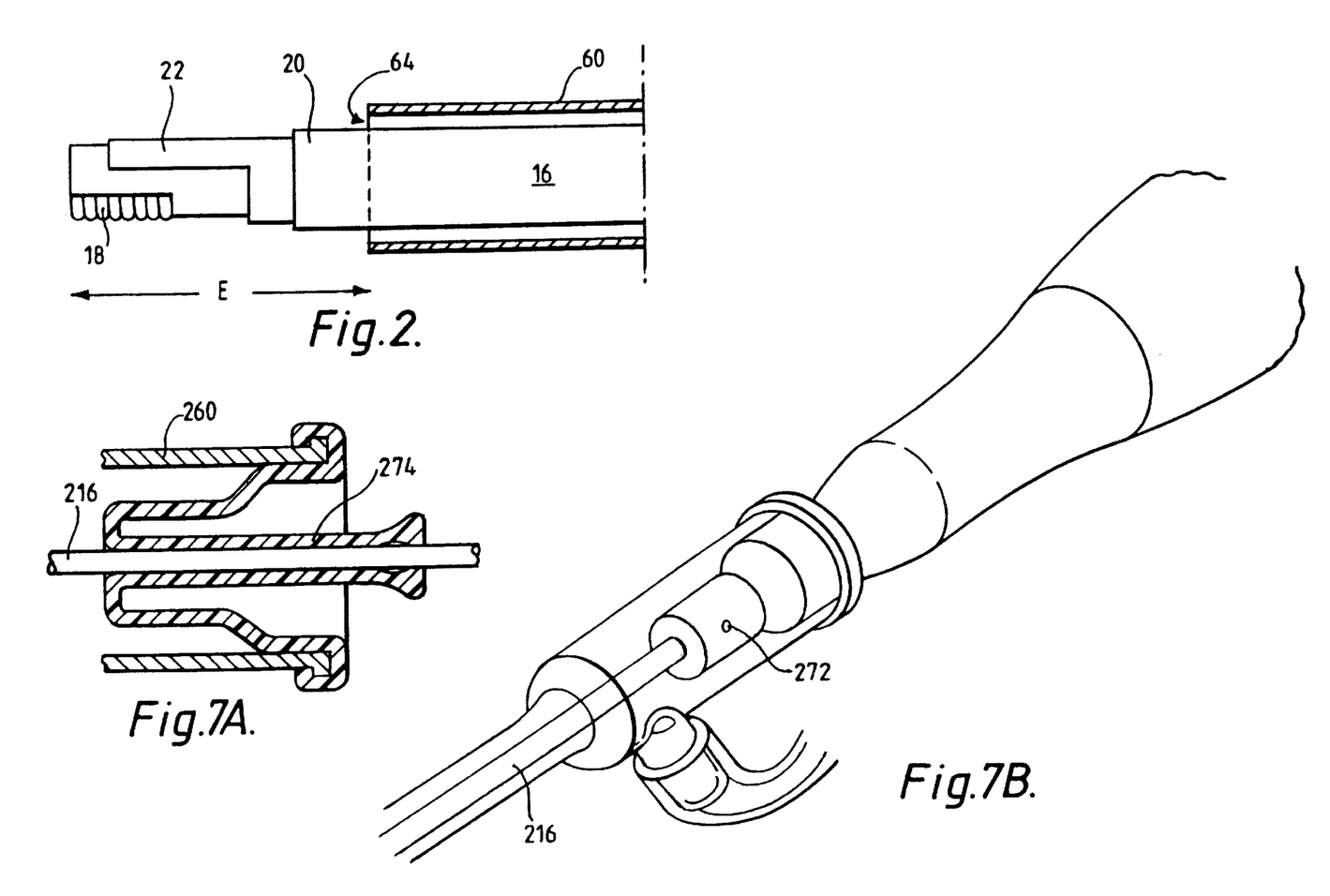
FIG. 2 is a detail of FIG. 1.
FIGS. 7A and 7B show a modification to the detail of FIG. 6.

Referring now to FIGS. 1 and 2, an electrosurgical generator (not shown) supplies RF power to an electrosurgical instrument 12. The instrument 12 has a handle 14 from which a shaft 16 extends, the shaft supporting an active electrode 18 which is axially spaced from the handle and which is located at the distal end of the shaft. A return electrode 20, also connected to the generator, is provided on the shaft 16 and is insulated from the active electrode 18 by means of a ceramic insulator 22. Depending upon the nature of the procedure to be performed with the instrument, access to the treatment site may be achieved in a number ways. For example, where the instrument is to be used to perform an arthroscopic procedure (i.e. a surgical procedure on a joint such as the shoulder or the knee), a technique known as triangulation is employed. This involves making two spaced-apart holes in the patient, and inserting the instrument through one of the holes, and a tube (known as a cannula) through the other, by means of which electrically-conductive fluid (typically isotonic saline) may be supplied to the treatment site, and which is also used to enable a fibre-optic viewing device to be positioned adjacent to the treatment site.

In one mode of operation, radio frequency current passing through the saline between the active and return electrodes 18, 20 causes the saline in the region of the active electrode to boil, resulting in the creation of a vapour pocket around the active electrode, and consequential arcing between the active and return electrodes across the boundary of the vapour pocket. By rapid and precise feedback control of the generator, the output power may be regulated such that the vapour pocket is maintained without destroying the electrodes 18 and 20. In this mode of operation, the instrument may be used to vaporise tissue by manipulating the instrument so that tissue encroaches within the vapour pocket, and is vaporised by the arcing which occurs between the electrodes 18 and 20 at its boundary. Details of the construction and operation of the instrument 12 and the generator 10 are known per se, and are described in our prior published International patent application WO 97/48345 and our prior published European patent application EP 0 754 437 (the contents of which are hereby incorporated by reference).

A by-product of the operation of the instrument in vaporisation mode is that it creates bubbles within the fluid which, in conjunction with debris from the vaporisation process, may obscure the surgeon's view of the treatment site, as provided by the remote viewing device which extends within the cannula. To provide for the removal of bubbles and/or debris, a sheath 50 is provided which is used to create a low pressure region in the vicinity of the active electrode 18, and thereby provide suction to remove bubbles and/or debris. The sheath 50 comprises an elongate flexible tube 60 which is made of a translucent material and has a relatively large opening 62 at its proximal end by means of which the instrument 12 may be inserted, and a smaller opening 64 at its distal end which allows the active electrode 18 to project out of the sheath 50, thereby enabling the active electrode to access tissue. An outlet port 66 is provided in the wall of the tube 60, and is connected to a suction pump (not shown) via a conduit 68 (here having the form of a flexible tube), to provide suction at the distal opening 64 of the tube. In order that most of the suction provided at the outlet port 66 is translated into suction at the distal opening 64, a seal is provided proximally of the outlet port, in the form of a sealing ring 72 which extends around the interior of the large proximal opening 62 in the tube 60. The sealing ring 72 abuts against a distal surface 74 on the instrument handle 14 to form a substantially fluid-tight seal, i.e. the integrity of the seal ensures that a substantial amount of the pressure reduction provided at the outlet port 66 appears at the distal opening 64, and therefore has the effect of sucking bubbles and or debris away from the treatment site, rather than sucking air into the interior of the tube.

Preferably, the sheath 50 is made of a relatively flexible material, and polymers having good meltflow properties are preferred since they enable it to be moulded. Preferable materials include: low density polyethylene; high density polyethylene; polypropylene; plasticised polyvinylchloride; polyurethane; poyether blockamide and some forms of thermoplastic elastomers. In each case, the material employed should preferably be stable under gamma radiation to enable this form of sterilisation to take place, and sufficiently flexible to enable the requisite degree of deformation to take place, either to accommodate an instrument with a crooked shaft, for example, or deformation which may occur when the distal end of the shaft is brought into a confined cavity.

As can be seen from FIG. 1, the diameter of the tube 60 is greater in the region of the outlet port 66 than at the distal end 64, which, although not essential, has a number of advantages. Firstly, the relatively narrow distal end of the sheath 50 improves access to confined treatment sites; and secondly, for a given flow rate of air demanded at the outlet port 66 by the suction pump, the relatively narrow distal opening 64 provides a higher pressure drop between the interior of the sheath and the fluid filled environment external to the sheath.

A further independent aspect of the present invention includes a sheath for an electrosurgical instrument comprising an elongate tube having an opening at a distal end through which an active electrode of the instrument may project, and a further opening at a proximal end to enable insertion of the instrument within the sheath, the sheath further comprising an outlet port via which suction may be applied to the interior of the tube, and sealing means located proximally of the outlet port, wherein the internal cross-sectional area of the tube is greater in the region of the outlet port than at the distal opening.

The flow rate of liquid over the surface of the active electrode 18 should be sufficiently low to prevent the consequent continual refreshment of liquid adjacent to the surface of the active electrode from removing heat from the active electrode so rapidly that the vapour pocket is quenched, since such a condition would result in the electrode becoming ineffective for vaporisation of tissue. The flow rate over the surface of the active electrode 18 may be regulated by adjusting the relative positions of the distal opening 64 and the active electrode 18, since, for a given flow rate of liquid through the distal opening, less liquid flows over the surface of the active electrode as the distance between the distal opening and the active electrode increases. Thus, in theory, an excessive flow rate of liquid through the distal opening 64, which could cause quenching of the vapour pocket can, within limits, be offset by an increased distance between the distal opening and the active electrode 18.

However, frequently in practice it is advantageous to operate with the lowest flow rate of liquid passing through the distal opening 64 which achieves the removal of bubbles and/or debris from the viewing line of the surgeon, and in practice flow rates of between 200 and 400 mls/min are usually employed. This is because firstly the pump which provides suction at the outlet port 66 will, in practice, usually be able to provide only a relatively low flow rate. In addition, the electrosurgical system in connection with which the sheath 50 is exemplified requires the presence of electrically-conductive fluid to operate. Thus, the flow rate of liquid sucked away from the treatment site must not exceed that of the flow rate of liquid supplied, and since liquid is frequently supplied under gravity from a reservoir or header tank located higher than the treatment site, the available supply pressure and flow rate of liquid supplied to the treatment site has practical limitations. In addition, it is sometimes desirable to distend the cavity in which the surgical procedure is to be performed in order to improve access to the treatment site, and this is usually achieved by pressurising the cavity using the electrically-conductive fluid, which in turn places limits on the permissible flow rate of fluid away from the treatment site. For these reasons, the flow rate of fluid through the distal opening 64 is generally known in advance to within fairly narrow limits, and given this it is generally desirable to regulate the flow rate of fluid passing over the surface of the active electrode 18 by setting the distance between the distal opening and the active electrode.

Referring now specifically to FIG. 2, to achieve this effect, the sheath 50 is preferably designed so that its length L (see FIG. 1) is such that, when an abutment on the sheath comes into contact with a corresponding abutment on the instrument, the distance E between the distal opening and the active electrode 18 is such (having regard to the flow rate of the suction pump and the power dissipated at the active electrode) as to provide a low enough flow rate over the surface of the active electrode to prevent quenching of the vapour pocket, and yet is sufficiently close to the active electrode to remove the requisite amount of bubbles and/or debris. In a preferred embodiment, the distance E is in the range of 3 to 6 mm, and more preferably is 4 to 5 mm for an output power of in the region of 100 Watts and flow rates of between 200 and 400 ml/min through the distal opening.

In the embodiment of FIG. 1, the abutment is conveniently provided by the seal between the sealing ring 72 on the sheath 50 and the proximal surface 74 of the instrument 12, but alternative forms of abutment are possible, such as an interior member within the tube 60 of the sheath which cooperates with a projection on the shaft 16 of the instrument, or a specially-configured detent mechanism between a series of slots formed in the proximal end of the tube and a lug provided on an adaptor mounted on the shaft, for example.

Accordingly, a further independent aspect of the present invention provides a sheath for an electrosurgical instrument comprising a flexible tube having a opening at a distal end through which an active electrode of the instrument may project, and a further opening at a proximal end thereof by means of which the instrument may be inserted therein, the sheath further comprising an outlet port and sealing means located proximally of the outlet port, the sealing means being cooperable with the instrument to cause suction applied at the outlet port to create low pressure at the opening.

Referring now additionally to FIGS. 3 to 5, a flow regulator 80 is provided on the flexible tube 68. The regulator 80 may, for example, have the form of a pinch clamp 82 (FIG. 3) or a screw clamp 84 (FIG. 4) in order to provide variable flow control, or alternatively may be provided by means of a valve enabling only "on" or "off" operation, such as by means of a slide valve 86 (FIG. 5). Typically, during normal operation, variations in the flow rate are only infrequently required since, as explained above, the positioning of the distal opening 64 of the sheath relative to the active electrode 18 provides optimum removal of bubbles and/or debris while preventing quenching of the vapour pocket around the active electrode. However, "on" or "off" operation is useful in avoiding, for example, wasting fluid during a hiatus in the surgical procedure.

Referring now to FIG. 6, an alternative form of seal 170 is illustrated. An internal web 172 extends transversely inside the tube 160 of the sheath, and forms a seal with the surface of the shaft 116 of the instrument 112. Location of the distal opening of the sheath relative to the active electrode of the instrument is still provided in this embodiment by abutment between the proximal end of the tube 160 of the sheath and the distal surface of the instrument handle. This form of seal has a number of advantages: firstly it enables different designs of instrument handle to be employed without regard for whether the distal surface thereof will be suitable for forming a seal with the proximal end of the tube 160; and secondly it permits the sheath to be moved axially relative to the instrument without substantial detriment to the integrity of the seal. This can be useful in the event that the distal opening (not shown) becomes blocked by debris. By retracting the instrument 112 within the sheath until the clearance between the active electrode and the interior of the tube 160 is sufficiently large to enable the debris to pass along the lumen formed between the tube and the shaft 116 of the instrument, debris may rapidly be cleared without undue interruption to the surgical procedure. This is made possible by the continual provision of suction during retraction of the instrument 112 acting to pull the debris through the tube 160, which is in turn made possible by retaining the integrity of the seal during this operation.

Referring now to FIGS. 7A and 7B, a further alternative form of seal is illustrated, and is provided by an elastomeric diaphragm 272. The diaphragm 272 grips the shaft 216 of the instrument so that during retraction of the instrument within the sheath, a central sealing member 274 of the diaphragm continues to grip the shaft while the remainder of the diaphragm deforms; this is in contrast to the web of FIG. 5 which, for larger movements of the instrument, slides over the shaft during retraction.

Preferably, the sealing member 274 will be made of a material which provides not just a good sealing action (in a preferred embodiment the maximum leak rate of the seal is 5 mls/min) but also good friction between the shaft 216 and the sealing member (in particular with the embodiment of FIG. 6). In a preferred embodiment, the sealing member is made of silicone rubber and provides a repositioning force against the retracting action of the surgeon of at least 15 Newtons.

A further independent aspect of the present invention provides a sheath for an electrosurgical instrument comprising an elongate tube into which the instrument is insertable, the tube having an opening at a proximal end to enable insertion of the instrument, and a further opening at a distal end thereof through which an active electrode of the instrument may project, and via which suction may be applied to a treatment site, the sheath further comprising a seal in the form of an internal member extending transversely to the tube and having a substantially central aperture through which an instrument shaft may project, and an outlet port located between the member and the distal opening.

Retraction of the sheath relative to the instrument may still be performed with the seal of the embodiment of FIG. 1 simply by the surgeon pinching the proximal end of the tube 60 sufficiently close to the instrument shaft to maintain a sufficient seal to provide the requisite suction to displace debris or other detritus along the internal lumen once the instrument is retracted. Ideally, the tube 60 will be made of translucent material, and preferably transparent material so that any blockages are easily visible to the surgeon.

Yet a further independent aspect of the present invention provides a sheath for an electrosurgical instrument comprising a translucent tube having an opening in a distal end thereof through which an active electrode of an instrument may project, a further opening at a proximal end by means of which an instrument may be inserted therein, an outlet port by means of which suction may be applied to the interior of the tube, and sealing means located proximally of the outlet port which causes suction applied at the outlet port to result in a low pressure at the distal opening.

Figure 8:
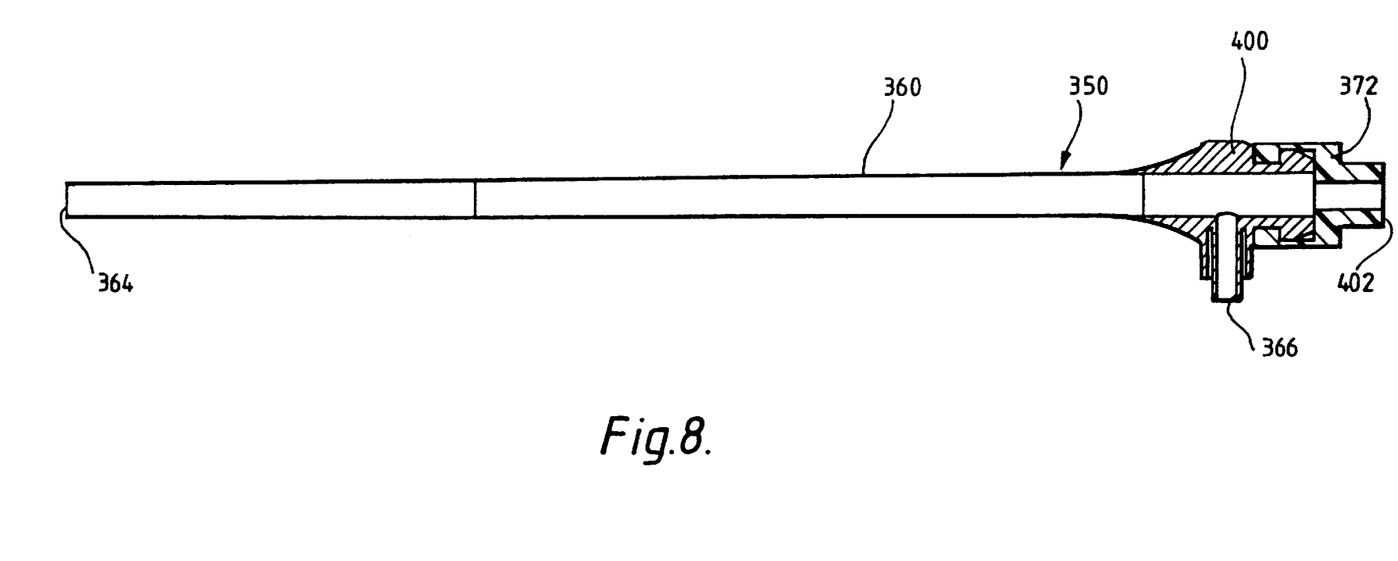
FIG. 8 is a section through a further alternative design of sheath.

The sheath of FIG. 1 can be seen to comprise three distinct sections of different diameters, from the relatively large diameter section adjacent to the outlet port 66 to the narrow diameter section in the region of the active electrode 18. An alternative design of tube for the sheath will now be described with reference to FIG. 8. Referring now to FIG. 8, a sheath 350 comprises an elongate tube 360 having a continuously-tapered cross-section. The tube 360 has, at its proximal end, a frusto-conical section by means of which it mates with a connecting member 400. The connecting member 400 incorporates an outlet port 366 by means of which suction may be applied to the interior of the sheath. Additionally, a flexible sealing member 372 is mounted to the rear of the connecting member 400, and, in use, the sealing member will cooperate with the instrument shaft (not shown in this drawing) to maintain a seal against the ingress of air within the sheath (other than that which enters in the form of bubbles at the distal end).

In addition, the rear face 402 of the sealing member will form an abutment against the distal end of the instrument handle thereby to locate the distal opening 364 at the requisite distance from the active electrode.

The various modifications and alternatives disclosed in the present application are not intended to be limited to their association with the embodiment in connection with which they were described. All of the various modifications and alternatives are applicable to any of the embodiments disclosed.

What is claimed is:

1. An electrosurgical system comprising an electrosurgical instrument having a handle defining a proximal end of the instrument and by means of which the instrument may be manipulated by a user, a shaft extending from the handle; and an active tissue treatment electrode on the shaft which is axially spaced from the handle and which defines a distal end of the instrument; the system further comprising an elongate removable sheath adapted to extend coaxially with, and externally around, the shaft of the instrument, the sheath comprising an outlet port, an opening on the distal side of the outlet port, and sealing means on the proximal side of the outlet port for forming a substantially fluid-tight seal with the instrument, thereby to enable low pressure applied at the outlet port to be transmitted to the distal opening to create suction in the region thereof, wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area and that extends a majority of the distance between the outlet port and the distal opening.

2. An electrosurgical system according to claim 1, wherein the sheath has a larger internal cross-sectional area adjacent to the outlet port than at the distal opening.

3. An electrosurgical system according to claim 1, further comprising a valve for regulating suction at the outlet port.

4. An electrosurgical system according to claim 1, wherein the sealing means includes a sealing member located within the sheath and extending transversely to the shaft of the instrument, the sealing member having a substantially central aperture through which the shaft of the instrument projects, and forming a substantially fluid-tight seal with the shaft.

5. An electrosurgical system according to claim 4, wherein the member is made of an elastomeric material.

6. An electrosurgical system according to claim 1, further comprising an abutment including mutually-engageable surfaces in the instrument and the sheath, wherein when the mutually-engageable surfaces are in engagement, the distal opening of the sheath is located at a predetermined distance from the active electrode.

7. An electrosurgical system according to claim 6, wherein the mutually-engageable surfaces are at the proximal end of the sheath and the distal end of the handle.

8. An electrosurgical system according to claim 1, wherein the instrument further comprises a return electrode on the shaft and electrically insulated from the active electrode.

9. An electrosurgical system according to claim 1, wherein the intermediate section has a cross-sectional area that continuously tapers down from the second cross-sectional area adjacent to the outlet port to the first cross-sectional area adjacent to the distal opening.

10. An electrosurgical system according to claim 1, wherein the sealing means is such that the sheath is movable axially relative to the instrument while maintaining the integrity of the seal with the instrument.

11. An electrosurgical system according to claim 1, wherein the sheath tapers from the outlet port to the distal opening.

12. An electrosurgical system according to claim 1, wherein the sheath has a stepped internal cross-section.

13. An electrosurgical system comprising:
an electrosurgical instrument having a handle defining a proximal end of the instrument and by means of which the instrument may be manipulated by a user;
a shaft extending from the handle;
an active tissue treatment electrode on the shaft which is axially spaced from the handle and which defines a distal end of the instrument; and
an elongate removable sheath adapted to extend coaxially with, and externally around, the shaft of the instrument, the sheath comprising an outlet port, an opening on the distal side of the outlet port, and sealing means on the proximal side of the outlet port for forming a substantially fluid-tight seal with the instrument, thereby to enable low pressure applied at the outlet port to be transmitted to the distal opening to create suction in the region thereof;
wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area;
wherein the sealing means includes a sealing member located within the tube and extending transversely to the shaft of the instrument, the sealing member having a substantially central aperture through which the shaft of the instrument projects, and forming a substantially fluid-tight seal with the shaft; and
wherein the sealing member has the form of a web.

14. An electrosurgical system comprising:
an electrosurgical instrument having a handle defining a proximal end of the instrument and by means of which the instrument may be manipulated by a user;
a shaft extending from the handle;
an active tissue treatment electrode on the shaft which is axially spaced from the handle and which defines a distal end of the instrument; and
an elongate removable sheath adapted to extend coaxially with, and externally around, the shaft of the instrument, the sheath comprising an outlet port, an opening on the distal side of the outlet port, and sealing means on the proximal side of the outlet port for forming a substantially fluid-tight seal with the instrument, thereby to enable low pressure applied at the outlet port to be transmitted to the distal opening to create suction in the region thereof;
wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area;

wherein the sealing means includes a sealing member located within the tube and extending transversely to the shaft of the instrument, the sealing member having a substantially central aperture through which the shaft of the instrument projects, and forming a substantially fluid-tight seal with the shaft; and wherein the sealing member has the form of a diaphragm.

15. An electrosurgical system comprising:

an electrosurgical instrument having a handle defining a proximal end of the instrument and by means of which the instrument may be manipulated by a user;

a shaft extending from the handle;

an active tissue treatment electrode on the shaft which is axially spaced from the handle and which defines a distal end of the instrument;

an elongate removable sheath adapted to extend coaxially with, and externally around, the shaft of the instrument, the sheath comprising an outlet port, an opening on the distal side of the outlet port; and sealing means on the proximal side of the outlet port for forming a substantially fluid-tight seal with the instrument, thereby to enable low pressure applied at the outlet port to be transmitted to the distal opening to create suction in the region thereof;

wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area; and wherein the sealing means includes a sealing ring located at the proximal end of the sheath, the sealing ring cooperating with a distal surface on the handle of the instrument to form a seal.

16. An electrosurgical system comprising:

an electrosurgical instrument having a handle defining a proximal end of the instrument and by means of which the instrument may be manipulated by a user;

a shaft extending from the handle;

an active tissue treatment electrode on the shaft which is axially spaced from the handle and which defines a distal end of the instrument; and an elongate removable sheath adapted to extend coaxially with, and externally around, the shaft of the instrument, the sheath comprising an outlet port, an opening on the distal side of the outlet port; and sealing means on the proximal side of the outlet port for forming a substantially fluid-tight seal with the instrument, thereby to enable low pressure applied at the outlet port to be transmitted to the distal opening to create suction in the region thereof;

wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area; and wherein the sheath is made of a translucent material.

17. An electrosurgical system comprising:

an electrosurgical instrument having a handle defining a proximal end of the instrument and by means of which the instrument may be manipulated by a user;

a shaft extending from the handle;

an active tissue treatment electrode on the shaft which is axially spaced from the handle and which defines a distal end of the instrument;

an elongate removable sheath adapted to extend coaxially with, and externally around, the shaft of the instrument, the sheath comprising an outlet port, an opening on the distal side of the outlet port, and sealing means on the proximal side of the outlet port for forming a substantially fluid-tight seal with the instrument, thereby to enable low pressure applied at the outlet port to be transmitted to the distal opening to create suction in the region thereof; and an abutment including mutually-engageable surfaces in the instrument and the sheath, wherein when the mutually-engageable surfaces are in engagement, the distal opening of the sheath is located at a predetermined distance from the active electrode;

wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area;

wherein the mutually-engageable surfaces are at the proximal end of the sheath and the distal end of the handle; and wherein the mutually-engageable surfaces are a sealing ring located at the proximal end of the sheath and a distal surface on the handle, the sealing ring and the distal surface forming the sealing means.

18. A method of operating an electrosurgical system comprising an electrosurgical instrument having a handle at a proximal end thereof by means of which the instrument may be manipulated, a shaft extending from the handle on which an active tissue treatment electrode is located at a distal end of the instrument, and an electrosurgical generator connected to the active electrode to supply radio frequency power thereto, the method comprising the steps of:

sheathing at least a part of the shaft of the instrument in a substantially fluid-tight chamber, the chamber having an opening located in the vicinity of the active electrode;

immersing the active electrode and thereby the opening within a liquid;

operating the generator to apply radio frequency power to the active electrode, thereby to create bubbles in the liquid; and reducing pressure within the chamber, thereby creating suction at the opening in the region of the active electrode and removing bubbles from the liquid.

19. A method according to claim 18, wherein the liquid is an electrically-conductive liquid, the method further comprising the steps of:

controlling the output power of the generator to form a vapour pocket around the active electrode; and controlling a flow rate of liquid over the surface of the active electrode occurring as a result of suction at the opening to ensure removal of bubbles from the vicinity of the active electrode, and simultaneously preventing heat removal from the active electrode sufficient to cause quenching of the vapour pocket.

20. A method according to claim 19, wherein the flow rate is controlled by the step of locating the opening at a predetermined distance from the active electrode.

21. A method according to claim 18, wherein the fluid-tight chamber has a larger internal cross-sectional area at its proximal end than at its distal end, the method further comprising the step of retracting the instrument within the sheath to increase a cross-sectional area of a lumen formed between a distal end of the instrument shaft and the chamber while maintaining suction at the opening of the chamber, thereby to enable the passage of any detritus blocking the lumen away from the opening and towards an outlet port in the chamber.

22. A method according to claim 21, wherein the suction at the opening is maintained during retraction of the instrument by virtue of a seal between the instrument shaft and a part of the chamber located proximally of the outlet port.

23. A sheath for an electrosurgical instrument, the sheath comprising an elongate tube having an opening at a distal end through which an active electrode of the instrument may project, and a further opening at a proximal end to enable insertion of the instrument within the sheath, the sheath further comprising an outlet port via which suction may be applied to the interior of the tube and sealing means located proximally of the outlet port, the sealing means comprising a member within the tube having a substantially central aperture through which a shaft of the instrument on which the active electrode is located may project, the member being adapted to form a substantially fluid-tight seal against the shaft, thereby to enable suction applied to the interior of the tube at the outlet port to create suction at the distal opening of the sheath, wherein the tube has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area and that extends a majority of the distance between the outlet port and the distal opening.

24. A sheath according to claim 23, wherein the internal cross-sectional area of the tube is greater in the region of the outlet port than at the distal opening.

25. A sheath for an electrosurgical instrument, the sheath comprising an elongate tube having an opening at a distal end through which an active electrode of the instrument may project, and a further opening at a proximal end to enable insertion of the instrument within the sheath, the sheath further comprising an outlet port via which suction may be applied to the interior of the tube, and sealing means located proximally of the outlet port, the sealing means comprising a member within the tube having a substantially central aperture through which a shaft of the instrument on which the active electrode is located may project, the member being adapted to form a substantially fluid-tight seal against the shaft, thereby to enable suction applied to the interior of the tube at the outlet port to create suction at the distal opening of the sheath, wherein the tube has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area, and wherein the sheath is made of a translucent flexible material.

26. An electrosurgical system according to claim 25, wherein the sheath tapers from the outlet port to the distal opening.

27. An electrosurgical system according to claim 25, wherein the sheath has a stepped internal cross-section.

28. An electrosurgical system comprising:

an electrosurgical instrument having a handle defining a proximal end of the instrument and by means of which the instrument may be manipulated by a user;

a shaft extending from the handle;

an active tissue treatment electrode on the shaft which is axially spaced from the handle and which defines a distal end of the instrument; and an elongate removable sheath adapted to extend coaxially with, and externally around, the shaft of the instrument, the sheath comprising an outlet port, an opening on the distal side of the outlet port, and sealing means on the proximal side of the outlet port for forming a substantially fluid-tight seal with the instrument, thereby to enable low pressure applied at the outlet port to be transmitted to the distal opening to create suction in the region thereof;

wherein the sheath has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area; and wherein the intermediate section includes a first section having the first cross-sectional area, a second section having the second cross-sectional area, and a third section extending axially between the first section and the second section having a third cross-sectional area that is greater than the first cross-sectional area, but smaller than the second cross-sectional area, the third section having an axial length greater than the axial length of either the first section or the second section.

29. A sheath for an electrosurgical instrument, the sheath comprising an elongate tube having an opening at a distal end through which an active electrode of the instrument may project, and a further opening at a proximal end to enable insertion of the instrument within the sheath, the sheath further comprising an outlet port via which suction may be applied to the interior of the tube and sealing means located proximally of the outlet port, the sealing means comprising a member within the tube having a substantially central aperture through which a shaft of the instrument on which the active electrode is located may project, the member being adapted to form a substantially fluid-tight seal against the shaft, thereby to enable suction applied to the interior of the tube at the outlet port to create suction at the distal opening of the sheath, wherein the tube has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area; and wherein the intermediate section includes a first section having the first cross-sectional area, a second section having the second cross-sectional area, and a third section extending axially between the first section and the second section having a third cross-sectional area that is greater than the first cross-sectional area, but smaller than the second cross-sectional are, the third section having an axial length greater than the axial length of either the first section or the second section.

30. A sheath for an electrosurgical instrument, the sheath comprising an elongate tube having an opening at a distal end through which an active electrode of the instrument may project, and a further opening at a proximal end to enable insertion of the instrument within the sheath, the sheath further comprising an outlet port via which suction may be applied to the interior of the tube and sealing means located proximally of the outlet port, the sealing means comprising a member within the tube having a substantially central aperture through which a shaft of the instrument on which the active electrode is located may project, the member being adapted to form a substantially fluid-tight seal against the shaft, thereby to enable suction applied to the interior of the tube at the outlet port to create suction at the distal opening of the sheath, wherein the tube has a first cross-sectional area adjacent to the distal opening, a second cross-sectional area larger than the first cross-sectional area adjacent to the outlet port, and an intermediate section extending axially between the first cross-sectional area and the second cross-sectional area, at least the majority of the intermediate section having an intermediate cross-sectional area that is greater than the first cross-sectional area and smaller than the second cross-sectional area, and wherein the intermediate section has a cross-sectional area that continuously tapers down from the second cross-sectional area adjacent to the outlet port to the first cross-sectional area adjacent to the distal opening.

* * * * *